(12) United States Patent
Sackett

(10) Patent No.: US 9,970,876 B2
(45) Date of Patent: May 15, 2018

(54) DUAL SOURCE ANALYZER WITH SINGLE DETECTOR

(75) Inventor: Donald W. Sackett, Bedford, MA (US)

(73) Assignee: SciAps, Inc., Woburn, MA (US)

( * ) Notice: Subject to any disclaimer, the term of this patent is extended or adjusted under 35 U.S.C. 154(b) by 937 days.

(21) Appl. No.: 13/591,907

(22) Filed: Aug. 22, 2012

(65) Prior Publication Data

US 2014/0022532 A1    Jan. 23, 2014

Related U.S. Application Data

(63) Continuation-in-part of application No. 13/507,654, filed on Jul. 17, 2012.

(51) Int. Cl.
| | |
|---|---|
| *G01J 3/42* | (2006.01) |
| *G01N 21/65* | (2006.01) |
| *G01J 3/44* | (2006.01) |
| *G01J 3/02* | (2006.01) |
| *G01J 3/18* | (2006.01) |
| *G01J 3/28* | (2006.01) |
| *G01J 3/443* | (2006.01) |
| *G01N 21/359* | (2014.01) |

(Continued)

(52) U.S. Cl.
CPC ............ *G01N 21/65* (2013.01); *G01J 3/0208* (2013.01); *G01J 3/0227* (2013.01); *G01J 3/18* (2013.01); *G01J 3/2803* (2013.01); *G01J 3/44* (2013.01); *G01J 3/443* (2013.01); *G01N 21/359* (2013.01); *G01N 21/718* (2013.01); *G01N 21/274* (2013.01)

(58) Field of Classification Search
CPC .. G01N 21/35; G01N 21/3563; G01N 21/359; G01N 21/6402; G01J 3/42; G01J 3/44; G01J 3/427

USPC ........... 250/282, 281, 338.1, 339.07, 339.11; 356/51, 301

See application file for complete search history.

(56) References Cited

U.S. PATENT DOCUMENTS

| | | | |
|---|---|---|---|
| 6,801,595 B2 | 10/2004 | Grodzins et al. | |
| 7,088,435 B2 * | 8/2006 | Brestel et al. | 356/72 |
| 7,233,643 B2 | 6/2007 | Sipila et al. | |

(Continued)

OTHER PUBLICATIONS

Written Opinion of the International Searching Authority; PCT Application No. PCT/US13/55706, dated Jan. 29, 2014 (ten (10) pgs (unnumbered)).

*Primary Examiner* — David Porta
*Assistant Examiner* — Djura Malevic
(74) *Attorney, Agent, or Firm* — Iandiorio Teska & Coleman, LLP

(57) ABSTRACT

A dual source system and method includes a high power laser used to determine elements in a sample and a lower power device used to determine compounds present in the sample. An optical subsystem directs photons from a sample to a detector subsystem after laser energy from the laser strikes the sample along an optical path. After energy from the device strikes the sample protons are directed to the detector subsystem along the same optical path. The detector subsystem receives photons after laser energy from the laser strikes the sample and provides a first signal, and receives photons after energy from the device strikes the sample and provides a second signal. A controller subsystem pulses the high power laser and processes the first signal to determine elements present in the sample, energizes the lower power device and processes the second signal to determine compounds present in the sample.

38 Claims, 6 Drawing Sheets

(51) Int. Cl.
*G01N 21/71* (2006.01)
*G01N 21/27* (2006.01)

(56) References Cited

U.S. PATENT DOCUMENTS

| | | | |
|---|---|---|---|
| 7,359,040 B1* | 4/2008 | Pendell-Jones et al. | 356/73 |
| 7,430,274 B2 | 9/2008 | Connors et al. | |
| 7,448,801 B2 | 11/2008 | Oettinger et al. | |
| 7,448,802 B2 | 11/2008 | Oettinger et al. | |
| 7,692,775 B2* | 4/2010 | Treado et al. | 356/73 |
| 7,924,414 B2* | 4/2011 | Mound | 356/73 |
| 7,945,393 B2* | 5/2011 | Treado et al. | 702/19 |
| 7,999,928 B2 | 8/2011 | Beckstead et al. | |
| 8,112,248 B2* | 2/2012 | Schweitzer et al. | 702/181 |
| 8,159,662 B2* | 4/2012 | Rezac et al. | 356/301 |
| 8,355,126 B2 | 1/2013 | Goulter et al. | |
| 2006/0256330 A1* | 11/2006 | Leipertz | 356/301 |
| 2006/0262304 A1* | 11/2006 | Carron | 356/328 |
| 2007/0153268 A1* | 7/2007 | Panza et al. | 356/301 |
| 2007/0192035 A1* | 8/2007 | Schweitzer et al. | 702/19 |
| 2008/0198365 A1* | 8/2008 | Treado et al. | 356/73 |
| 2008/0268548 A1* | 10/2008 | Zuckerman | 436/172 |
| 2008/0300826 A1* | 12/2008 | Schweitzer et al. | 702/181 |
| 2009/0001262 A1 | 1/2009 | Visser et al. | |
| 2009/0012723 A1* | 1/2009 | Treado et al. | 702/28 |
| 2009/0066947 A1* | 3/2009 | Bangalore et al. | 356/317 |
| 2009/0101843 A1* | 4/2009 | Henshaw et al. | 250/484.4 |
| 2009/0163369 A1* | 6/2009 | Treado et al. | 506/8 |
| 2010/0171951 A1 | 7/2010 | Misra et al. | |
| 2010/0182594 A1* | 7/2010 | Carron | 356/73 |
| 2011/0080577 A1* | 4/2011 | Nelson et al. | 356/73 |
| 2011/0237446 A1* | 9/2011 | Treado et al. | 506/8 |
| 2012/0034686 A1 | 2/2012 | Berlin et al. | |
| 2012/0062697 A1* | 3/2012 | Treado et al. | 348/42 |
| 2012/0062873 A1* | 3/2012 | Stewart et al. | 356/72 |
| 2012/0147358 A1* | 6/2012 | Gardner et al. | 356/72 |
| 2013/0188181 A1* | 7/2013 | Angel et al. | 356/301 |
| 2014/0204377 A1 | 7/2014 | Day et al. | |

* cited by examiner

Table 1: Example of the Calibration Method Utilizing Elemental and Compound Measurements

| Element | Intensity | Calibration Constant $K_1$ | Concentration % (Universal Cal) $\% = K_1 *$Intensity | Correction Factor to Universal calibration F (Using Raman Result) | Revised Calibration Constant (K') $K_1' + K_1 * F$ | Revised Concentration (%) $\%' + K_f *$Intensity |
|---|---|---|---|---|---|---|
| Al | 50,000 | 4.6800E-07 | 2.34% | 1.14 | 5.3352E-07 | 2.67% |
| Si | 75,000 | 1.6400E-06 | 12.30% | 1.34 | 2.1976E-06 | 16.48% |
| Cr | 4,500 | 1.2444E-07 | 0.06% | 0.88 | 1.0951E-07 | 0.05% |
| H | 110,000 | 1.6182E-07 | 1.78% | 0.73 | 1.1813E-07 | 1.30% |
| Mn | 145,000 | 4.6207E-08 | 0.67% | 1.05 | 4.8517E-08 | 0.70% |
| Fe | 94,000 | 7.8887E-06 | 74.15% | 1.22 | 9.6242E-06 | 90.47% |
| O | 134,000 | 6.4925E-07 | 8.70% | 0.91 | 5.9082E-07 | 7.92% |

*FIG. 4*

DUAL SOURCE ANALYZER WITH SINGLE DETECTOR

RELATED APPLICATIONS

This application is a continuation-in-part of U.S. patent application Ser. No. 13/507,654 filed Jul. 17, 2012 and claims the benefit of and priority thereto under 35 U.S.C. §§ 119, 120, 363, 365, and 37 C.F.R. § 1.55 and § 1.78 and is incorporated herein by this reference.

FIELD OF THE INVENTION

The subject invention relates to spectroscopic instruments.

BACKGROUND OF THE INVENTION

Spectroscopic instruments are fairly well known. X-ray based instruments, for example, can be used to determine the elemental make up of a sample using x-ray florescence spectroscopy. Portable XRF has become a preferred technique for elemental analysis in the field. Portable XRF is fast, non-destructive, and provides reasonably accurate results (i.e., quantification of elemental concentrations in a wide variety of samples). With XRF, an x-ray tube is used to direct x-rays at a sample. Atoms in the sample absorb x-rays and re-emit x-rays that are unique to the atomic structure of a given element. A detector measures the energy of each x-ray and counts the total number of x-rays produced at a given energy. From this information, the types of elements and the concentration of each element can be deduced. Commercially available analyzers include the Delta manufactured by Olympus NDT and the Niton XLT-3 manufactured by Thermo Fisher Scientific.

X-rays, however, pose a safety concern. Also, portable and benchtop XRF analyzers have not to date measured beryllium (Be), boron (B), carbon (C), lithium (Li), oxygen (O), nitrogen (N), and the like.

Laser induced break down spectroscopy (LIBS) devices are known and used to detect the elemental concentration of lower atomic numbered elements with some accuracy. These devices typically include a high powered laser that sufficiently heats a portion of the sample to produce a plasma. As the plasma cools, eventually the electrons return to their ground states. In the process, photons are emitted at wavelengths unique to the specific elements comprising the sample. The photon detection and subsequent measurement of elemental concentrations are very similar to spark optical emission spectroscopy (OES). Examples of LIBS devices are the LIBS SCAN 25 from Applied Photonics, the LIBS25000 from Ocean Optics, and the RT 100 from Applied Spectra.

Still other instruments are better at determining the molecular compositions present in a sample. Portable, laser based Raman spectrometers or a wide bandwidth based (i.e., non-laser) near infra-red (NIR) analyzers can be used. These devices are configured to collect either Raman spectra or infra-red absorption from a given sample. They then compare the acquired spectra to a library of spectra of pure compounds. From the comparisons, the devices then determine the major compounds present in the sample. The process of determining what combination of pure compounds spectra in published libraries yield the measured spectrum of an unknown mixture is called chemometrics. There are several commercially available portable devices utilizing Raman technology including those manufactured by Thermo Fisher Scientific, Delta Nu and B&W Tek. For NIR, commercially available devices are made by ASD, Thetino Fisher Scientific, and Spectral Evolution.

Portable Raman and NIR analyzers are able to identify compounds present in a mixture, but they are generally limited to identifying what main compounds are present (as opposed to how much of each compound is present), or, at best, they can provide an approximate quantification of only a few components in a mixture of compounds. This limitation is due to sample response variation as a function of particle size, particle density, and mixture type, whether it be a solid solution or an inhomogeneous mixture of compounds. These parameters can cause the spectrum from one material to be enhanced or reduced relative to the other materials to a fair extent. In addition, both the Raman and NIR methods are sensitive to material very near the sample surface so that any variation is bulk vs. surface concentrations will be missed. Even without these effects, the ability to derive chemical constituents from mathematically combining spectra of pure compounds to simulate the unknown mixture spectrum rapidly degrades after the third compound, even with good quality spectra. In addition, currently available portable Raman and NIR units typically require a good deal of spectral interpretation from the operator, thus limiting user community to more technical users.

It is also known to fuse the data in dual source systems. That is, for example, Raman spectra data and LIBS spectra data are obtained and software is configured to calculate probability values to pinpoint an unknown material like a microorganism. See for example, published U.S. Patent Application Nos. 2009/0163369 and 2011/0080577 and U.S. Pat. No. 7,999,928 all incorporated herein by this reference. Some of these designs are expensive and complex (using, for example, a FAST spectrometer and fiber optic bundles.)

Still, LIBS spectroscopy, for example, can produce inaccurate elemental concentrations in some cases and Raman and NIR spectroscopy can report one or more inaccurate compositions, mainly because for many compounds, the Raman or NIR spectra produced by those compounds are very similar. Plus, some libraries contain more than 10,000 spectra from the many compounds. Fusing the data may not improve accuracy.

SUMMARY OF THE INVENTION

Featured is a novel portable (e.g., handheld, or easily transportable benchtop or shoulder pack style) instrument that combines measurement from two technologies (e.g., LIBS and Raman or LIBS and NIR) with an analysis algorithm that allows operators to quantify both elements and compounds. Knowledge about the compounds present in the sample enables the method to better report the elemental concentrations. Knowledge about the elemental concentrations enables the method to better quantify the compounds present.

In addition, the use of the LIBS measurement for elemental concentrations allows a more refined searching of large libraries of pure compound spectra used for NIR and Raman analysis. Therefore, the chemometrics process is also improved via a novel method since the elements present are measured in the sample from LIBS and only compounds comprised of those measured elements can be present in the sample. The knowledge of elemental concentrations thus greatly reduces and refines the library searches for Raman or NIR analysis.

Another unique feature of the method is that the analytical results are internally consistent and satisfy expected mass balances and constraint equations. This means the total concentration of a given element measured from LIBS will agree with the stoichiometric and molecular composition results from all the compounds that contain that element as determined by the Raman or NIR analysis.

Also, if trace compounds present in the sample are not detected in the Raman or NIR analysis, then detection of an element using LIBS and knowledge of other compounds actually detected by the Raman or NIR analysis allows the reporting of the trace compounds.

Featured is a dual source system comprising a high power (e.g., LIBS) laser used to determine elements in a sample and a lower power device (e.g., Raman laser) used to determine compounds present in the sample. An optical subsystem is preferably configured to direct photons from the sample to a detector subsystem after laser energy from the high powered laser strikes the sample along an optical path and to direct photons from the sample to the detector subsystem after energy from the lower powered device strikes the sample along the same optical path.

The detector subsystem may be configured to receive photons via the optical subsystem from the sample after laser energy from the high power laser strikes the sample and provides a first signal. The detector subsystem also receives photons, via the optical subsystem, after energy from the lower powered device strikes the sample and provides a second signal.

A controller subsystem is preferably configured to pulse the high power laser and process the first signal to determine one or more elementals present in the sample and to energize the lower power device and process the second signal to determine one or more compounds present in the signal.

The optical subsystem may further be configured to direct electromagnetic energy from the lower power device to the sample along an optical path including at least a portion of the optical path from the sample to the detector subsystem. The optical subsystem can also be designed to direct electromagnetic energy from the high power laser to the sample along an optical path including at least a portion of the optical path from the sample to the detector subsystem.

In one example, the lower power device outputs energy at a predetermined wavelength and the optical subsystem includes an optical component receiving energy output by the lower power device and configured to direct said energy to the sample. The optical component may receive photons from the sample and can be configured to filter wavelengths in a narrow band about a predetermined wavelength and to direct energy in wide bands above and below the narrow band to the detection subsystem. In one embodiment, the optical component includes a dichroic notch reflector configured to reflect energy from the lower power device to the sample and to transmit energy in wide bands to the detector subsystem. Or, the reflector can be configured to transmit energy from the lower power device to the sample and to reflect energy in the wide bands to the detector subsystem. One optical subsystem further includes a lens positioned such that photons from the sample after energy from the lower power energy device strikes the sample are received at and focused by the lens. Photons from the sample after energy from the high power device strike the sample are also received and focused by the same lens. The focusing lens can also be positioned to focus energy from the lower power device onto the sample.

In some examples, the controller subsystem is configured to determine one or more elemental concentrations in the sample based on the first signal and to quantify one or more compounds present in the sample based the one or more elemental concentrations determined to be present in the sample.

The controller subsystem can be further configured to adjust the measured elemental concentrations based on the determined compounds. In one example, determining one or more elemental concentrations includes using one or more calibration constants and adjusting the elemental concentrations includes using different calibration constants based on the compounds present in the sample. Quantifying a compound in the sample can include using a concentration of an element unique to a compound in order to determine the concentration of the compound. The controller subsystem can be further configured to compare the determined elemental concentrations with elemental concentrations of the defined compound concentrations using mass/balance equations. The controller subsystem can also be configured to quantify concentrations using elements shared among two or more compounds. Also, or in addition, the controller subsystem can be configured to report one or more additional compounds present in the sample based on the elemental concentrations and the one or more determined compounds.

In some examples, the high power laser source is configured for LIBS spectroscopy and the lower power device is a laser configured for Raman spectroscopy. In other examples, the lower power device is a near infrared source for near infra-red absorption measurements.

Also featured is a dual source system comprising a high power laser used to determine elements present in a sample, a lower power device used to determine compounds present in a sample, a detector subsystem configured to receive photons from the sample, and an optical path from the sample to the detector subsystem for the elemental determination the same as the optical path for the compound determination. In some examples, an optical path from the lower power device to the sample includes at least a portion of the optical path from the sample to the detector subsystem and/or an optical path from the high power laser to the sample includes at least a portion of the optical path from the sample to the detector subsystem.

One dual source system includes a high power laser used to determine elements present in a sample, a lower power device used to determine compounds present in a sample, a detector subsystem configured to receive photons from the sample, and a first optical path from the high power laser to the sample at least partially co-linear with a second optical path from the lower power device to the sample. In some examples, an optical path from the sample to the detector subsystem is at least partially co-linear with the first and second optical paths.

Also featured is a method comprising directing photons from a sample, after impingement of high and low power energy at the sample, via the same optical path from the sample to a detector subsystem and directing lower power energy to the sample via an optical path including at least a portion of the optical path from the sample to the detector subsystem. The method may further include directing higher power energy to the sample via an optical path including at least a portion of the optical path from the sample to the detector subsystem.

Also featured is a method comprising directing lower power energy to a sample via an optical path, directing high power energy to the sample via an optical path at least partially co-linear with the optical path for the lower power energy, and directing photons from the sample after impingement of high and low power energy at the sample to a detector subsystem. The method may further include directing photons from the sample after impingement of high and low power energy at the sample via the same optical path from the sample to the detector subsystem.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 4 is a schematic view showing a calibration method in accordance with examples of the invention.

DETAILED DESCRIPTION OF THE INVENTION

Figure 1:
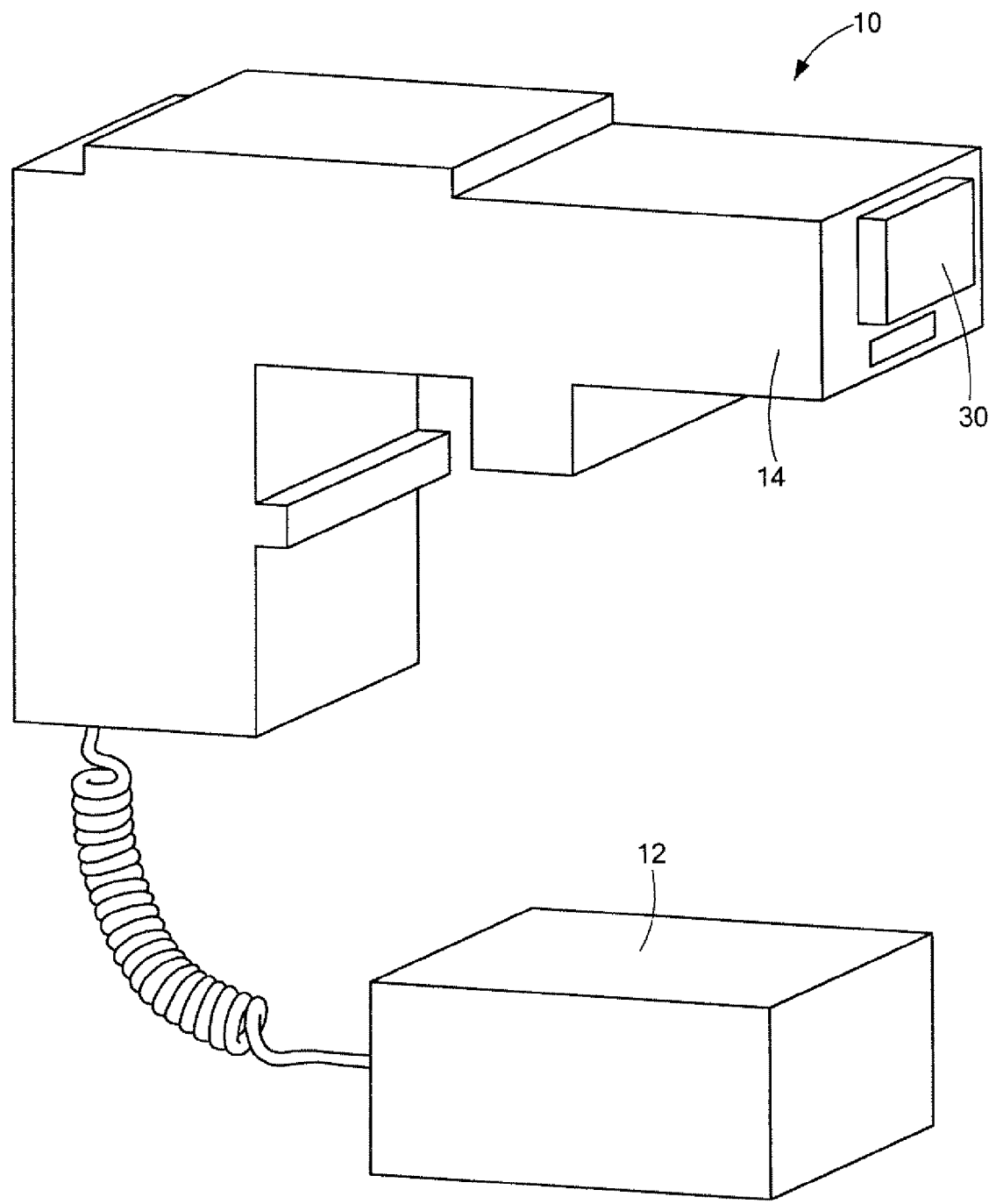
FIG. 1 shows a schematic three dimensional view showing an example of a portable handheld instrument in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows a version of a portable, hand held dual source device 10 embodying an example of the invention. In one design, device 10 may include separate belt or shoulder mounted power pack 12. Housing 14 typically houses a high power laser 16, FIG. 2 used in a LIBS analysis to determine elemental concentration in sample 18. Lower power laser 20 may be used in a Raman analysis to determine compounds present in sample 18. Alternately, an NIR (infrared absorption) subsystem could be used.

Laser energy from laser 16 (e.g., 1064 nm) and energy from source 20 (e.g., 785 nm) exit window 30 FIG. 1 via optics such as focusing lenses 32a and 32b, FIG. 2 and also beam splitter 34. Photons from the sample are returned to the device via the window 30 and are received at detector subsystem 40 via beam splitter 34, lens 32c, and notch filter 42. A collimating optic 44, grating 46, and focusing optic 48 can be used to direct the photons to CCD detector array 50 which outputs signals to controller subsystem 52.

For LIBS analysis, the signals represent intensities at different wavelengths defining the elements in the sample and the concentration of each of those elements. For a Raman (or NIR) analysis, the signals result from molecular group vibrations and are thus characteristic of molecular compounds present in the sample.

Various libraries may be stored in memory 54 accessed by controller subsystem 52. Various mass balance equations, calibrations constants, and the like may also be stored in memory 54 as disclosed below.

Controller subsystem 52 may include one or more microprocessors, digital signal processors, or similar components, and/or application specific integrated circuit devices, and may be distributed e.g., one microprocessor can be associated with the detector subsystem 40 while another microcontroller can be associated with the device's electronic circuit board(s). The same is true with respect to the algorithms, software, firmware, and the like. The various electronic signal processing and/or conditioning and/or triggering circuitry and chip sets are not depicted in the figures.

In general, the processor subsystem 52 is configured (e.g., programmed) to pulse high power laser 16 and process the resulting signals from detector subsystem 40 to determine one or more elemental concentrations in sample 18. Controller subsystem 52 then energizes lower power source 20 and processes the resulting signals from detector subsystem 40 to determine one or more compounds present in the sample. Knowing the elements present enables a more efficient determination of the compounds present. Then, based on the one or more compounds present in the sample, controller subsystem 52 can be configured to adjust the concentrations previously determined, although this step is optional. Finally, controller subsystem 52 is configured to quantify the one or ore compounds of the sample using the elemental concentration data. Knowing both the elemental concentrations and compound concentrations enables a more accurate result.

In this particular design, the Raman laser delivery optics is combined with the spectrometer or detection subsystem optics while the LIBS laser delivery optics are independent. Both measurements preferably use the same detection subsystem for emission analysis.

Figure 2A:
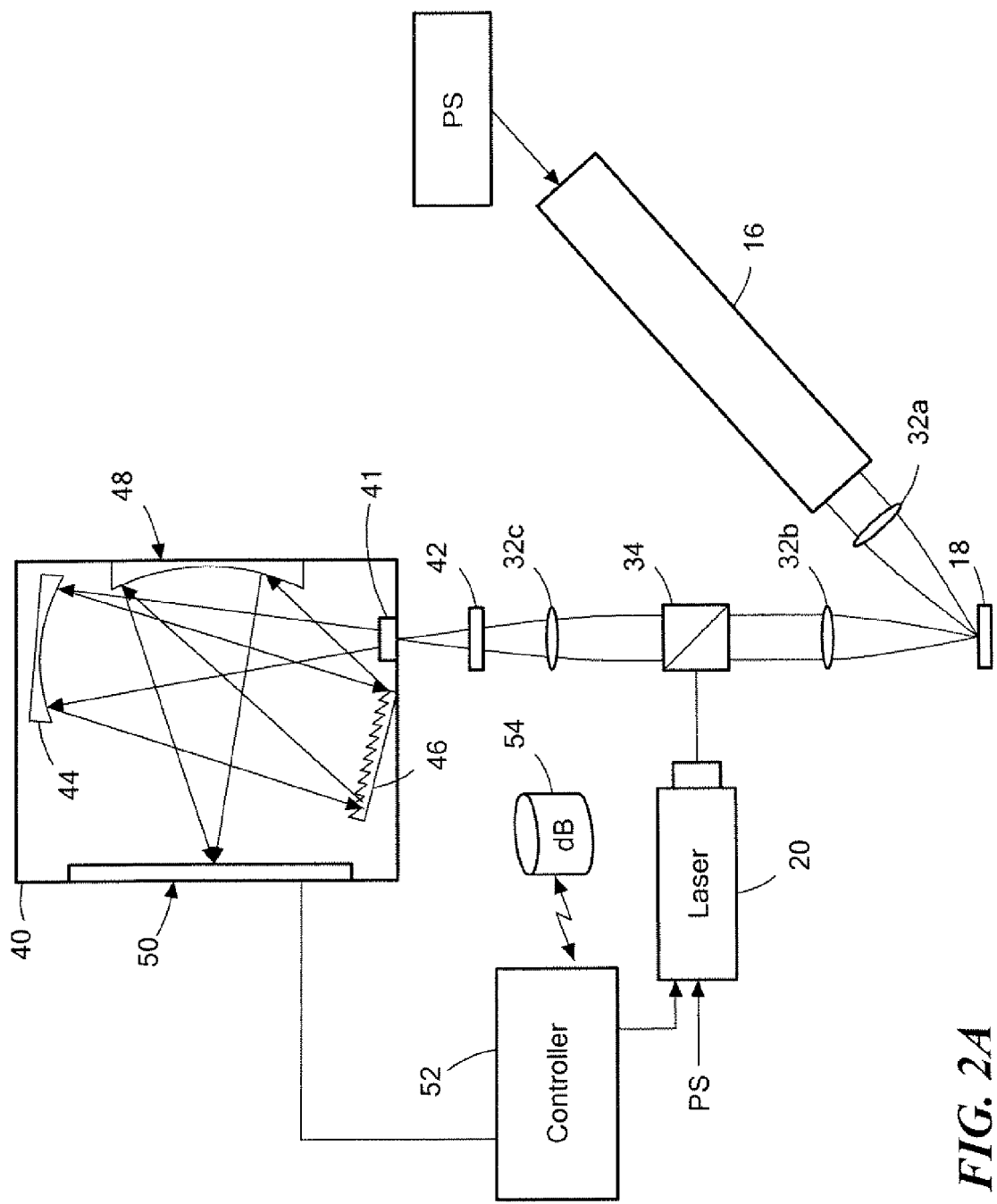
FIG. 2A is a schematic block diagram showing the primary components associated with the portable instrument of FIG. 1.

The illuminated sample area during the Raman measurement is on the order of 20-100 um while the plasma generated by the LIBS laser in on the order of 1000 um or more. In order for the detection optics to be properly aligned with the small Raman illumination area, it is advantageous if they are co-linear and share the same focusing optics. In FIG. 2A it can be seen that if the sample is not perfectly located at the focus of lens 32b, light from a small illuminated area will still make it back to detection subsystem 40. On the other hand, if the same sample is out of position vertically, the LIBS laser 16 will hit the sample slightly offset from the detection optics focus. Since, however, the LIBS plasma is large (1 mm or so), portions of the plasma will still be within the detection optics view and make it to the detector subsystem 40 (e.g., a spectrometer).

Energy from laser 20 is directed toward optical component 34, typically a dichroic notch reflector. Optical component 34 reflects only a narrow band of wavelengths including that of laser 20 (typically 785 nm). Optical component 34 directs collimated laser light through focusing lens 32b to a small spot on the sample. The resulting Raman signal, shifted in the wavelength (e.g., 810-1040 nm), is emitted in all directions from the sample. Light that intercepts lens 32b is recollimated. Since the Raman signals are wavelength shifted, they will pass through optical component 34 on toward detection subsystem 40 passing through re-focusing lens 32c and an optional notch filter 42 designed to reject light in a narrow band surrounding the laser wavelength (e.g., 785 nm). The Raman signal is typically 6-9 orders of magnitude smaller than the excitation laser wavelength and so a similar degree of filtering may be required to prevent the laser signal from overwhelming the very small Raman signals.

Photons resulting after energy from laser 20 strikes the sample thus pass through optical component 34 in wide bands above and below the narrow band filtered by component 34. In one example, component 34 filters wavelengths in a narrow band of between about 760-780 nm. Raman wavelengths from the sample 18 from about 790 to 1500 nm pass through filter 34.

The focus of lens 32c directs the Raman light onto slit 41 of detector subsystem 40. The size of slit 41 is a function of the spectrometer resolution. Inside detection subsystem 40, the light passing the slit is collimated by mirror 44 and then directed toward diffraction grating 46. The diffraction grating reflects the light such that each wavelength leaves the grating at a slightly different angle. Focusing mirror 48 causes each wavelength to be focused onto detector array 50 such that each wavelength would be shifted to different segments of the detector array resulting in the measured spectrum. Other spectrometer implementations are possible including Echell (with a 2D CCD), Paschen-Runge, and the like. A spectrometer which yields high resolution over a wide band of wavelengths (e.g., 200 nm-1000 nm) is preferred.

During operation of LIBS laser 16, the Raman laser 20 is typically turned off and the LIBS laser 16 is pulsed in either a single burst or train of bursts. Light leaving the resulting generated plasma formed on sample 18 follows the same detection path namely lens 32b, component 34, lens 32c, optional filter 42, and slit 41. LIBS wavelengths in the wide band ranges of about 180 nm-760 nm and about 780 nm-1500 nm are transmitted by component 34. Plasma emissions in the narrow band are filtered by component 34 and do not reach detection subsystem 40 but this is such a small fraction of the available LIBS spectrum that it has little determent to the wealth of information available.

Figure 2B:
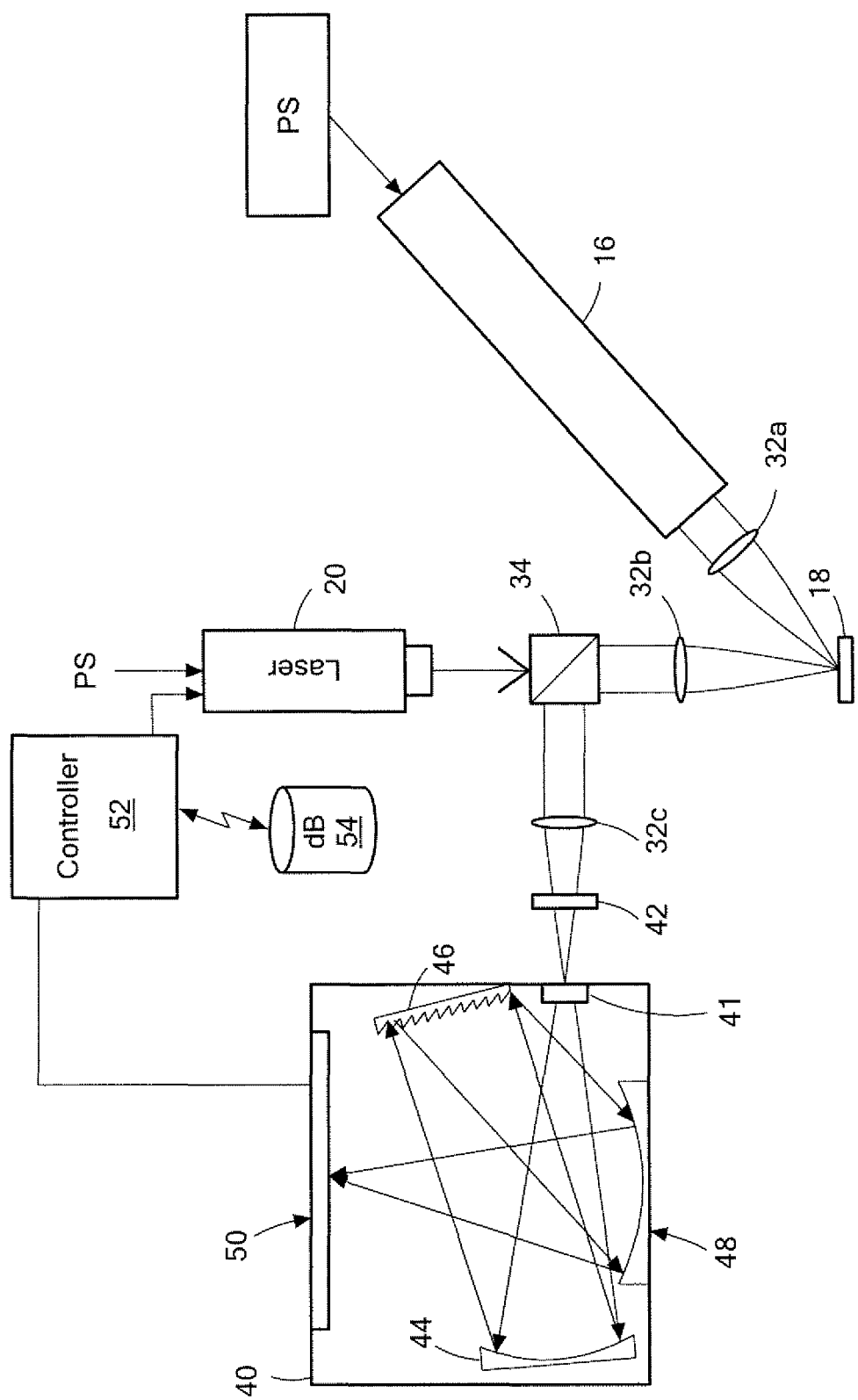
FIG. 2B is a block diagram of another example of the invention.

In another implementation, shown in FIG. 2B, wavelengths from the Raman and LIBS laser are redirected (reflected) by component 34 as shown to detector subsystem 40 while the Raman laser is positioned such that laser energy is transmitted through optical component 34.

So far, the optical path from the sample to the spectrometer (also called the return path) is the same for both the LIBS and Raman generated photons, the optical path from the Raman laser to the sample includes a portion of the optical path from the sample to the spectrometer, and the optical path from the LIBS laser to the sample is direct to the sample.

Other embodiments can be enabled. In one example the optical path from the LIBS laser to the sample also includes a portion of the optical path from the sample to the spectrometer.

Figure 2D:
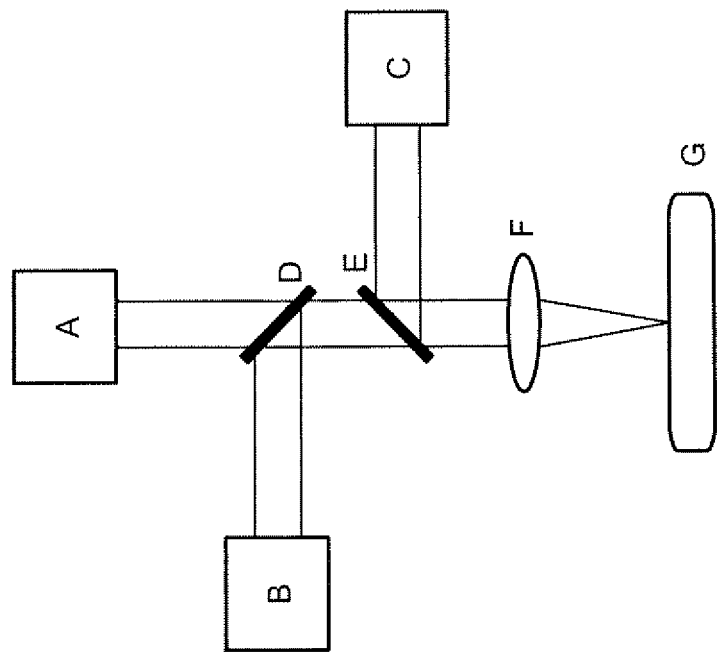
FIG. 2D is a block diagram depicting additional examples.
Figure 2C:
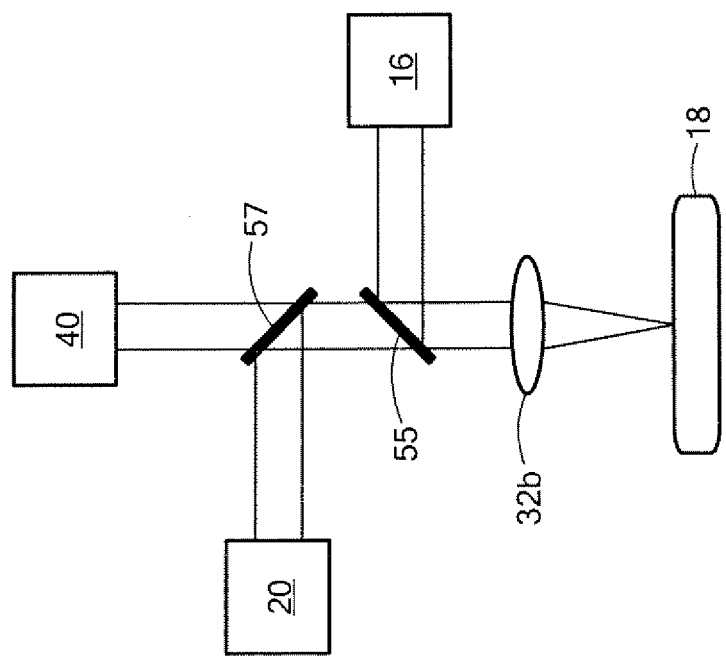
FIG. 2C is a block diagram of another example.

FIG. 2C, for example, shows an embodiment where the return optical path from the sample 18 to spectrometer 40 includes lens 32b and low pass filter 55 which transmits all wavelengths below that of the LIBS laser 16 (e.g., below about 1040 nm for a 1064 LIDS laser). Also included in the return optical path is notch filter 57 which transmits wavelengths except in a narrow band around the wavelength of the Raman laser 20.

The optical path for the Raman laser 20 includes notch filter 57 and low pass filter 55 which reflects a narrow band surrounding the Raman wavelength and directs this band to low pass filter 55 which transmits the narrow band to sample 18. So, the optical path for the Raman laser 20 to the sample includes a portion of the return optical path.

The optical path for the LIBS laser includes low pass filter 55 which reflects wavelengths above (e.g., above about 1050 nm) a wavelength near the wavelength (e.g., 1064) of LIBS laser 16 and directs them to sample 18. Thus, the optical path for the LIBS laser now also includes a portion of the return optical path.

By choosing the correct filters, the positions of the spectrometer, the Raman laser and LIBS laser can vary as shown in the following chart referring to FIG. 2D:

| Configuration | A | B | C | D | E |
|---|---|---|---|---|---|
| 1 | S | RL | LL | NF | LP |
| 2 | S | LL | RL | LP | NF |
| 3 | RL | S | LL | BPF | LP |
| 4 | LL | S | RL | HP | NF |
| 5 | RL | LL | S | | |
| 6 | LL | RL | S | | |

| Key: | |
|---|---|
| S | Spectrometer |
| RL | Raman Laser |
| LL | LIBS Laser |
| NF | Notch Filter |
| BPF | Band Pass Filter |
| HP | High Pass Filter |
| LP | Low Pass Filter |

One preferred notch filter reflects light in a narrow band closely surrounding the Raman wavelength and transmits approximately 100% of wavelengths in wide bands above and below the narrow band. One preferred band pass filter transmits only a very narrow band closely surrounding the Raman laser wavelength and reflects or otherwise filters approximately 100% of wavelengths in wide bands above and below the narrow band. One preferred high pass filter transmits all wavelengths above a threshold (e.g., 1040 nm) and filters approximately 100% of all wavelengths below that threshold value. One preferred low pass filter transmits all wavelengths below the threshold value and reflects or otherwise filters all wavelengths above the threshold. Other filters, thresholds, and bands could be used for other laser(s) or source wavelengths are within the scope of the subject invention.

By juxtapositioning all three beam paths (Raman laser excitation, LIBS laser excitation, and spectrometer detection) at the output optics, several advantages are realized.

The juxtaposed geometry helps insure that the focus of the two lasers and spectrometer all occur at the same point on the sample. Additionally, this configuration is significantly more tolerant of samples slightly distanced from the ideal focal point. Also, LIBS measurements typically result in sample cratering and the superposition of the Raman and LIBS spectrometer beam paths insure that the bottom of the crater can be continuously viewed regardless of depth. In all the designs discussed so far, additional filters and/or optical components may be required for additional laser line rejection. Depending on the spectrometer type used, it may additionally contain a focusing lens to focus the collimated beam onto a spectrometer slit.

Figure 3:
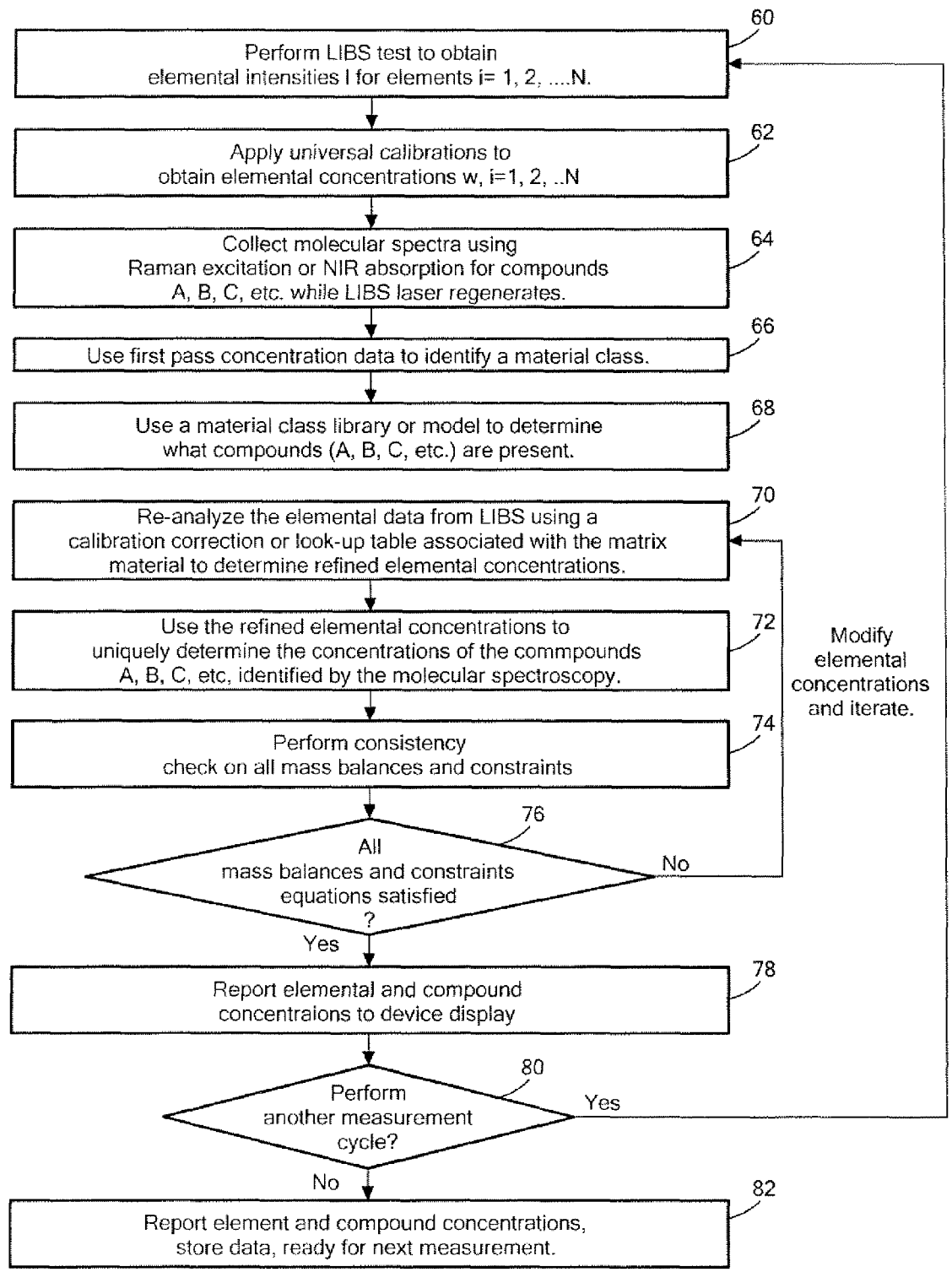
FIG. 3 is a flow chart depicting the primary steps associated with a method in accordance with the invention and also associated with the programming of the microcontroller subsystem of FIG. 2.

A method of this invention, which can be implemented, for example, in the device of FIGS. 1 and 2 as algorithms in software, typically includes the steps depicted in FIG. 3. A LIBS measurement, step 60, measures the intensities of various wavelength of light from the various elements in the sample. The LIBS measurement is very fast, typically requiring a few microseconds of time. The laser 16, FIG. 2 is operated in a pulsed mode meaning the laser is turned on for about 4 to 10 nsec to heat sample 18 and thus create a plasma, then switched off. At the end of the laser pulse, there is typically a 1 to 10 microsecond delay while the plasma cools and before the settling of the excited electrons back to their original atomic states occurs. After that delay, the detection subsystem 40 begins acquiring atomic emission spectra. This spectral acquisition occurs for about another 1 to 2000 microseconds after which the LIBS measurement has concluded. Intensities at specific wavelengths that are characteristic of specific elements are measured at detector subsystem 40, FIG. 2.

In step 62, FIG. 3 these intensities, adjusted for background levels, are converted into concentration values ($W_i$ for element "I") preferably from a universal calibration. In general, for optical emission, the relation between concentration and measured light intensity can be adequately represented by either a quadratic or cubic polynomial. An example, for the case of measuring the element chromium (Cr) would be:

$$W_{Cr}=K_0+K_1 {*}I_{Cr}+K_2 {*}I_{Cr}^2 \qquad (1)$$

or $$K_{Cr}=K_0+K_1 {*}I_{Cr}+K_2 {*}I_{Cr}^2+K_3 {*}I_{Cr}^3 \qquad (2)$$

where $W_{Cr}$ is the concentration of Cr in mass %, $I_{Cr}$ is the intensity of light measured at the wavelength for chromium light emission from the plasma, and K0, K1, K2, and K3 are calibration coefficients stored in memory 54, FIG. 2. These calibration coefficients are determined from calibration where samples with known concentrations (W) at various levels are tested and the light intensity (I) emitted by each element of interest is measured. The values of W versus I are plotted for each element, fitted by a quadratic or cubic polynomial, thus yielding the coefficients of the quadratic or cubic polynomial. The coefficients are the calibration constants used for that particular type of sample. In this example, the type of sample may be the element Cr in an iron alloy type of sample.

In analytical measurements, the most accurate results are obtained when the calibration is tuned to the specific composition of the sample. For example, the best results when measuring Cr in an iron alloy is obtained when the calibration factors K0, K1, etc. are derived from a calibration using iron alloys with known amounts of chromium. However, the field sample composition is generally unknown so the best calibration coefficients are not known a priori. Instead, based on the elements that produce the highest intensity of measured photons, the sample composition is estimated and the best available calibration factors are automatically selected. If it is determined, for example that the sample is a nickel alloy, then different calibration constants (e.g., $K_0'$, $K_1'$, $K_2'$, and $K_3'$) stored in memory are chosen at step 62.

Step 64, FIG. 3 in the method is to turn on the molecular excitation source 20, FIG. 2 which is either a Raman laser or an NIR source (lamp), depending on whether the desired molecular measurement technique is Raman analysis or NIR absorption. During this time the LIBS laser 16 is allowed to regenerate so that a second LIBS pulse may be used later in the measurement. Molecular spectra are acquired from the sample. With knowledge of the compounds present, an improved estimate of the sample composition is now available. The controller subsystem can be configured to use the compound information to choose a more optimal set of calibration coefficients $K_0'$, $K_1'$, etc., from memory for each element, therefore allowing more precise measurements.

In step 66, FIG. 3 a library search is initiated and in step 68 a chemometrics process is used. Because of the complexity of the chemometrics process, thousands of similar spectra would have to be analyzed and combined in such a way as to match the measured spectrum from the mixture. But here the LIBS measurement has determined the total concentrations of elements present in the sample. This knowledge is valuable because it can be used in the searching algorithms to greatly limit the number of spectra that need be search and analyzed by the Raman or NIR chemometrics process. For example, any library compound (in memory 54, FIG. 2) can be ignored if it does not contain at least one of the elements measured by LIBS. This can greatly limit the number of possible compounds to consider in the chemometric analysis allowing for a more reliable determination of compounds present.

This is accomplished, for example, if a library search of either Raman or NIR spectra finds spectra from two different compounds that match the measured spectrum. However the compounds likely are comprised of different elements or different elemental concentrations. Because the LIBS measurement determines the elements present in the sample, one of the possible matches can be eliminated if that compound is comprised of elements not found by the LIBS measurement or if the elemental concentrations are significantly different. A good example is the case where LIBS measures total elemental concentrations Ca, Mg, C and O are present among others. An NIR measurement determines that the mineral could either be Dolomite [formula is $CaMg(CO_3)_2$] or simple Calcite [formula is $CaCo_3$)]. Because the LIBS measurement detected and determines total Mg present, the mineral can be uniquely identified as Dolomite because it contains Mg whereas Calcite does not.

With the compounds in the sample known, step 70, FIG. 3 is used to refine the choice of calibration coefficients for each element. In one example, in step 62, a default set of calibration constants K were chosen resulting in an output of 21% Cr. In step 68, the compound chromium chloride ($CrCl_3$) was determined to be present in the sample. Based on this determination, a new set of calibration constants K' are used resulting in an output of 19% Cr. In step 68, had the compound sodium Chromate ($Na_2CrO_4$) been present, a different set of calibration constants K" would have been automatically used resulting in 23% Cr.

One example of the calibration process is shown in FIG. 4. For simplicity a simple linear calibration is assumed, namely, $W_i=K{*}I_i$ for element (i). In Table 1, column 1 is the name of the element being analyzed and column 2 is the measured intensity of light for that element, in arbitrary units, measured from the spectrometer. Column 3 shows the result from Step 62, FIG. 3 where a general calibration is applied. The general calibration is typically chosen from a data table in memory 54, FIG. 2. The choice of calibration is dictated by what elements were measured with the largest intensities. For example, if a large amount of iron (Fe), silicon (Si) and oxygen (O) were measured along with other elements, then a calibration from an iron ore type of matrix would likely be chosen.

In steps 64-68, the Raman or NIR analysis is performed to determine what compounds are present in the sample at appreciable levels. The known elemental content is used to guide the search of the material library, as mentioned earlier. From the knowledge of the major compounds, the elemental calibration can be further refined. For example it may be determined that one compound is appreciable higher in concentration than others. In the above example it may be determined that a large amount of an organic compound or water is present. In this case there may be a better choice of elemental calibration constants than previously used or the calibration constants used must be corrected due to the presence of a previously unknown compound. For the example in FIG. 4, it is determined that a correction (F) to the calibration constants will produce a more accurate result. In this case, new calibration constants (K') are generated by multiplying the initial choice (K) by the correction factor (F). Improved elemental concentration results are then generated and reported by multiplying the measured intensities (I) of each element by the associated calibration constants (K'). In most cases, the adjusted calibration constant (K') will change by 10-50%.

A further step in the method would be to re-check the Raman or NIR materials library to see if the revised elemental concentrations determined from calibration constants K' alter the results of material library search for compounds present. It is expected that the minor changes to the elemental results will not impact the choice of compounds. If they do, then an iterative procedure can be used to eventually converge to a self-consistent result for both elemental concentrations and compounds present.

Steps 72-76 show an approach which uses the results of the elemental concentration data combined with the types of compounds present to yield quantitative compound concentrations ($P_j$). Moreover, the elemental and compound concentrations can be analyzed to ensure internal consistency, meaning mass balance equations are satisfied.

Steps 72-76 involve using the measured elemental concentrations from LIBS (steps 62, 70) and the determined compounds from Raman or NIR (step 68) to quantitatively determine the percentages of compounds present in this sample. Moreover, mass balances are used to also assure that the two independent measurements of elemental concentrations (LIBS) and compound concentrations (Raman or NIR) are self consistent. In most cases, the resulting system of equations is over-determined meaning there are more equations than unknowns. There may also be measurement uncertainties associated with each element measured by LIBS. This is a desirable outcome because standard mathematical techniques such as least squares can be used to find the best overall solution that meets the measured elemental concentrations (including uncertainties), the calculated compound concentrations and the stoichiometry associated with these compounds, and the overall mass balance equations.

For example, suppose there are four compounds present in a sample as determined at step 68, FIG. 3: Compound A=$SiO_2$, Compound B=$CaCO_3$. Compound D=$CH_2$ and Compound E=$Al_2O_3$. Note that in practicality the compounds $SiO_2$ and $Al_2O_3$ do not yield good NIR spectra but they are useful in this case to teach the method. In addition there are three free elements (free meaning they are not associated with any compound): Fe, Ni and Cu. The elemental concentrations are measured with LIBS and yields concentration values for all the elements present $W_{Fe}$, $W_{Ni}$, $W_{Cu}$, $W_{Si}$, $W_O$, $W_{Ca}$, $W_C$, $W_H$, and $W_{Al}$ step 62, FIG. 3.

The presence of the four compounds are determined by the Raman or the NIR measurement and the still unknown compound concentrations are denoted by $P_A$, $P_B$, $P_D$, and $P_E$. The concentration of the free elements Fe, Ni and Cu, and the concentration of the elements found only in one compound (Si, Ca, H and Al) are uniquely determined from the LIBS measurement. Here, the compounds in this example share two elements carbon and oxygen (the shared elements). The LIBS measurement provides total oxygen and total carbon concentration but it is not known from the LIBS measurement how much of the measured oxygen is in compound A, B or E. Similarly the LIBS measurement does not tell us how much of the measured carbon is in B versus D. The NIR or Raman measurement only provides presence of these compounds, but not concentrations.

In this example, each compound contains a unique element, meaning the element isn't found in any of the other compounds determined to be present in the sample. Using stoichiometry, the percentages of compounds A, B, D and E are given by:

$$P_A = a*W_{Si}, \quad (3)$$

where $a$=(molecular weight of $SiO_2$)/(molecular weight of Si)/(number of atoms of Si per atom of $SiO_2$). (4)

Here, the number of atoms of Si per atom of $SiO_2$ is equal to 1.

Also, $$P_B = b*W_{Ca}, \quad (5)$$

where $b$=(molecular weight of $CaCO_3$)/(molecular weight of Ca)/(number of atoms of Ca per atom of $CaCO_3$). (6)

Here the number of atoms of Ca per atom of $CaCO_3$ is equal to 1.

Similarly, $P_D = d*W_H$, (7)

where $d$=(molecular weight of $CH_2$)/(molecular weight of H)/(number of atoms of H per atom of $CH_2$). (8)

Here the number of atoms of H per atom of $CH_2$ is equal to 2.

Finally, $P_E = e*W_{Al}$ (9)

where $e$=(molecular weight of $Al_2O_3$)/(molecular weight of Al)/(number of atoms of Al per atom of $Al_2O_3$). (10)

Here the number of atoms of Al per atom of $Al_2O_3$ is equal to 2.

At this point in the method, the self consistency test (mentioned above) can be performed by applying the overall mass balance equations. In this example, the weight percentages P where determined for the four compounds using measured values of elements that were unique to the compound, i.e., elements not present in two or more compounds. The total weight percent of carbon and oxygen are also known from the LIBS measurement. From a mass balance, the elemental concentration of total oxygen, as measured by LIBS, must agree with the total oxygen expected from the percentages and stoichiometry of compounds A, B and E. Also the elemental concentration of total carbon, as measured by LIBS, must agree with the total carbon expected from the percentages and stoichiometry of compounds B and D. And, by definition the sum of all the compounds plus elements that are not molecularly bound in a compound must be 100%. The following mass balance equations ensue:

$$W_O = f*P_A + g*P_B + h*P_E \quad (11)$$

where $f=$(molecular weight of O)/(molecular weight of SiO$_2$)*(number of atoms of O per atom of SiO$_2$), (12)

$$g=\text{(molecular weight of O)/(molecular weight of CaCO}_3)\text{*(number of atoms of O per atom of CaCO}_3\text{), and} \quad (13)$$

$$h=\text{(molecular weight of O)/(molecular weight of Al}_2\text{O}_3)\text{*(number of atoms of O per atom of Al}_2\text{O}_3\text{).} \quad (14)$$

Also, $$W_C = i*P_B + j*P_D \quad (15)$$

where $i=$(molecular weight of C)/(molecular weight of CaCO$_3$)*(number of atoms of C per atom of CaCO$_3$) (16)

where $i=$(molecular weight of C)*(molecular weight of CH$_2$)*(number of atoms of C per atom of CH$_2$). (17)

Finally, $P_A + P_B + P_D + P_E + W_{Fe} + W_{Ni} + W_{Cu} = 100\%$ (18)

In this example, there are four unknowns (the concentrations of the four compounds) and there are seven equations including the mass balance equations. Each measured value of elemental concentrations (W) from LIBS will have a measurement uncertainty associated with it. There are standard mathematical techniques utilizing the method of least squares to solve over-determined systems of equations with statistical weights.

As another example, consider a sample with four compounds (CaS, CaSO$_4$, CaOH, and Fe$_2$O$_3$), plus several elements present only in the atomic form, (i.e., not part of a molecule) and iron (Fe) that is present both in atomic form in the sample and in the molecular form Fe$_2$O$_3$. This example is more complex than the previous because four elements measured by LIBS for total concentration are shared across multiple compounds (Ca, S, O and Fe). This example yields five unknown values and six equations. The five unknowns are the concentrations of the four compounds plus the concentration of the atomic iron (i.e., the iron not bound in the molecule Fe$_2$O$_3$). The six equations are given by mass balances for Ca, S, O, Fe and H, plus the requirement that the sum of the concentrations of all the compounds plus the elements in atomic form equals 100%.

In general, the solution will involve an over-determined system of linear equations and measurement uncertainties, making least squares with a convergence test after each iteration a favored approach. Provided there is at least one element that is unique to one of the compounds in the sample, the problem will yield an over-determined system of linear equations. In the first example, Si, Ca and Al were all unique to specific compounds in this example. In the second example, only hydrogen was unique.

Another example is a typical geochemical application. In this example, there are many metals in the sample and all reside in a mineralogical form that a user seeks to learn. Suppose there are multiple metals present in a sample. The LIBS measurement determines concentrations for Fe, Al, Si, Cu, Mg, Mn, C, H, N, O, Sr, Rb and Ti. The molecular measurement, likely NIR in this case rather than Raman, indicates the presence of compounds Fe$_2$O$_3$, Al$_2$O$_3$, SiO$_2$, CuO, MgO, Mn$_2$O$_5$, CH$_2$N (using a hypothetical organic compound as a teaching example). The levels of compounds containing Sr, Rb and Ti are trace and not detected by the NIR but the user knows they are there since the more sensitive LIBS measurement detected Sr, Rb and Ti. This example shows the power of the combined measurements of molecular and elemental concentrations, along with an algorithm to handle the combined data set. The concentrations of all the compounds detected by NIR can be determined from the LIBS measurement since the molecular form is known by the NIR measurement. There are additional equations for the organic compound because it uniquely contains H, C and N, all three of which are measured by total element concentration from LIBS. A mass balance on O yields an equation, and the requirement that the sum of all compounds and free element concentrations=100% yields a final equation. It is a safe assumption that the trace metals Sr, Rb and Ti are all in standard oxide form since the NIR measurement indicated oxide forms for all the other metals and the LIBS measurement provided the total concentration of Sr, Rb and Ti. With the assumption of oxide form for Sr, Rb and Ti, the concentrations of the compounds can be determined. Therefore, this is a system of equations with 10 unknown compounds, but 14 equations. This system of equations which is over-determined and with uncertainty weights on all the measured values is a prime candidate for a least squares minimization solution to the set of linear equations.

For example, it is well established that for portable Raman and NIR devices, it is very difficult to determine the presence of compounds with concentrations less than 0.5%. This is because these compounds make a very small contribution to the measured spectrum, since the measured spectrum is an aggregate of spectra from the various compounds in the sample. However if a LIBS measurement identifies the presence of trace metals that are not found in the compounds identified by the NIR or Raman measurement, then a finer analysis can be done using library spectra of only compounds containing those LIBS-detected elements. The search could be limited to a specific class of such compounds, such as oxides only. As an example, consider a case where LIBS measurement measures the presence of elements Na, H, Mg, Li, C, O, Si, Fe, Mn. The NIR measurement determines the only minerals present are Hectorite (containing Ma, Mg, Li, Li, O and H and iron oxide (Fe$_2$O$_3$). Then, it can be reasonably assumed that there are low levels K- and Mn-containing compounds present in the sample, likely K$_2$O and MnO. Those library spectra can be folded into the chemometrics process.

In step 78, FIG. 3 the concentration data is reported and stored. It is typical in most measurements, including LIBS, that performing a second cycle of a LIBS test, followed by an NIR or Raman test, will improve the precision of the measurement. Thus in step 80, the software will examine the current result, compared to the previous result, and either repeat the result or terminate the test depending the settings chosen by the operator, step 82.

In summary, one novel approach is to quantify both elements and compounds with a single preferably portable device by first measuring with LIBS to determine all elements present (using an assumed calibration) based on the relative intensities of elements measured, then performing a Raman or NIR test to determine what compounds are present, using the known elements from the LIBS measurement to refine the library search to improve the accuracy of compound determination, and, based on the knowledge of the major compounds, solve a system of (typically) over determined equations including mass balances to determine percentages of compounds, and possibly further refining the calibrations for the elemental analysis now that percentages of compounds are known. This solution process can be iterative until all the equations are satisfied.

There are other embodiments that can be envisioned as well. Portable XRF could be used to measure elemental concentrations instead of LIBS. However, XRF analysis is difficult for elements with atomic numbers less than Mg, and therefore C, O, N, Be, B and other common elements will not be measured. Also, the Raman or NIR measurement can be taken first, followed by the LIBS measurement. The combined LIBS+NIR or LIBS+Raman measurements can be taken once, meaning a single LIBS test of the sample followed by a Raman or NIR test, or multiple tests of each are possible. In general, multiple tests improve precision especially of the LIBS result but there is a point of diminishing returns where additional repeat tests do not appreciably improve the result.

Thus, featured via the steps of FIG. 3 is a computer implemented method comprising analyzing emission spectra from a sample to determine one or more elemental intensities at different wavelengths. The concentration of one or more elements present in the sample is calculated using the first set of calibration data. A molecular measurement technique is employed to determine one or more compounds present in the sample using the one or more elements determined to be in the sample. Based on the one or more compounds determined to be present in the sample, the concentrations of the one or more elements can be recalculated using an optional second set of calibration data. Based on the recalculated concentrations of the elements, and the compounds present in the sample are quantified. Mass balance equations can be used to recalculate the concentration of the elements and compounds. Also, one or more additional compounds can be reported based on trace elements determined to be in the sample and the other compounds found to be in the sample.

So, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A dual source handheld analysis system comprising:
   a high power laser used to determine elements in a sample;
   a lower power device used to determine compounds present in the sample;
   an optical subsystem including optical components and configured to:
   direct photons from the sample to a detector subsystem after laser energy from the high powered laser strikes the sample along an optical path,
   direct photons from the sample to the detector subsystem after energy from the lower powered device strikes the sample along said same optical path,
   direct photons from the high power laser to the sample via at least a portion of said optical path,
   direct photons from the lower power device to the sample via at least a portion of said optical path, and
   the detector subsystem configured to:
   receive photons via the optical subsystem from the sample after laser energy from the high power laser strikes the sample and providing a first signal, and
   receive photons via the optical subsystem after energy from the lower powered device strikes the sample and providing a second signal; and
   a controller subsystem configured to:
   pulse the high power laser and process the first signal to determine one or more elements present in the sample, and
   energize the lower power device and process the second signal to determine one or more compounds present in the sample.

2. The system of claim 1 in which the lower power device outputs energy at a predetermined wavelength and the optical subsystem includes an optical component receiving said energy at said predetermined wavelength output by the lower power device and configured to direct said energy at said predetermined wavelength to the sample.

3. The system of claim 2 in which said optical component further receives photons from the sample and is configured to filter wavelengths in a narrow band about said predetermined wavelength and to direct energy in wide bands above and below said narrow band to said detection subsystem.

4. The system of claim 3 in which said optical component includes a dichroic notch reflector.

5. The system of claim 4 in which said reflector is configured to reflect energy from the lower power device to said sample and to transmit energy in said wide bands to said detector subsystem.

6. The system of claim 4 in which said reflector is configured to transmit energy from the lower power device to said sample and to reflect energy in said wide bands to said detector subsystem.

7. The system of claim 1 in which said optical subsystem further includes a lens positioned such that photons from the sample after energy from the lower power energy device strike the sample are received at and focused by said lens and photons from the sample after energy from the high power device strikes the sample are received and focused by said lens.

8. The system of claim 7 in which said focusing lens is also positioned to focus energy from the lower power device onto the sample.

9. The system of claim 1 in which said controller subsystem is configured to determine one or more elemental concentrations in the sample based on the first signal.

10. The system of claim 9 in which said controller subsystem is further configured to quantify one or more compounds present in the sample based the one or more elemental concentrations determined to be present in the sample.

11. The system of claim 10 in which the controller subsystem is further configured to adjust the measured elemental concentrations based on the determined compounds.

12. The system of claim 11 in which the determining one or more elemental concentrations includes using one or more calibration constants and adjusting the elemental concentrations includes using different calibration constants based on the compounds present in the sample.

13. The system of claim 10 in which quantifying a compound in the sample includes using a concentration of an element unique to said compound to determine the concentration of said compound.

14. The system of claim 10 in which the controller subsystem is further configured to compare the determined elemental concentrations with elemental concentrations of the defined compound concentrations.

15. The system of claim 14 in which the comparison includes using mass/balance equations.

16. The system of claim 10 in which the controller subsystem is configured to quantify concentrations using elements shared among two or more compounds.

17. The system of claim 10 in which the controller subsystem is configured to report one or more additional compounds present in the sample based on the elemental concentrations and the one or more determined compounds.

18. The system of claim 1 in which the high power laser source is configured for LIBS spectroscopy.

19. The system of claim 1 in which the lower power device is a laser configured for Raman spectroscopy.

20. The system of claim 1 in which the lower power device is a near infrared source for near infra-red absorption measurements.

21. A dual source handheld analysis system comprising:
a high power laser used to determine elements present in a sample;
a lower power device used to determine compounds present in a sample;
a detector subsystem configured to receive photons from the sample;
an optical path from the sample to the detector subsystem for the elemental determination the same as the optical path for the compound determination; and
an optical path from the high power laser and the lower power device to the sample including at least a portion of the optical path from the sample to the detector subsystem.

22. The system of claim 21 in which the optical path from the sample to detector subsystem includes a first lens and a notch filter.

23. The system of claim 22 in which an optical path from the lower power device to the sample includes the notch filter positioned to direct energy from the lower power device to said first lens.

24. The system of claim 23 in which said optical path from the sample to the detector subsystem includes said filter positioned to direct wavelengths in wide bands above and below a narrow band to the detector subsystem.

25. The system of claim 21 further including a controller subsystem configured to determine one or more elements present in the sample after energy from the high power laser strikes the sample and to determine one or more compounds present in the sample after power from the lower power device strikes the sample.

26. The system of claim 25 in which the controller subsystem is further configured to determine elemental concentrations and to quantify one or more compounds present in the sample based on the determined elemental concentrations in the sample and the determined compounds present in the sample.

27. The system of claim 21 in which the high power laser source is configured for LIBS spectroscopy.

28. The system of claim 21 in which the lower power device is a laser configured for Raman spectroscopy.

29. The system of claim 21 in which the lower power device is a near infrared source for near infra-red absorption measurements.

30. A dual source handheld analysis system comprising:
a high power laser used to determine elements present in a sample;
a lower power device used to determine compounds present in a sample;
a detector subsystem configured to receive photons from the sample via a first optical path; and
a second optical path from the high power laser to the sample at least partially co-linear with a third optical path from the lower power device to the sample, the second and third optical paths including at least a portion of the first optical path.

31. The system of claim 30 in which the third optical path from the lower power device to the sample includes a notch filter positioned to direct energy from the lower power device to a first lens.

32. The system of claim 31 in which said first optical path from the sample to the detector subsystem includes said filter positioned to direct wavelengths in wide bands above and below a narrow band to the detector subsystem.

33. The system of claim 30 further including a controller subsystem configured to determine one or more elements present in the sample after energy from the high power laser strikes the sample and to determine one or more compounds present in the sample after power from the lower power device strikes the sample.

34. The system of claim 33 in which the controller subsystem is further configured to determine elemental concentrations and to quantify one or more compounds present in the sample based on the determined elemental concentrations in the sample and the determined compounds present in the sample.

35. The system of claim 30 in which the high power laser source is configured for LIBS spectroscopy.

36. The system of claim 30 in which the lower power device is a laser configured for Raman spectroscopy.

37. The system of claim 30 in which the lower power device is a near infrared source for near infra-red absorption measurements.

38. A dual source handheld analysis system comprising:
a high power laser used to determine elements in a sample and emitting a laser beam directed to a sample via a lens;
a lower power device used to determine compounds present in the sample and emitting a beam directed to the sample via said lens;
an optical subsystem configured to:
direct photons from the sample to a detector subsystem after laser energy from the high powered laser strikes the sample along an optical path including said lens; and
direct photons from the sample to the detector subsystem after energy from the lower powered device strikes the sample along said optical path including said lens;
the detector subsystem configured to:
receive photons via the optical subsystem from the sample after laser energy from the high power laser strikes the sample and providing a first signal, and receive photons via the optical subsystem after energy from the lower powered device strikes the sample and providing a second signal; and a controller subsystem configured to:
pulse the high power laser and process the first signal to determine one or more elements present in the sample, and energize the lower power device and process the second signal to determine one or more compounds present in the sample.

\* \* \* \* \*